United States Patent [19]

Shephard et al.

[11] Patent Number: 4,728,665
[45] Date of Patent: Mar. 1, 1988

[54] BENZOYLAMINOMETHYLPYRAZOLES AND FURANS, COMPOSITION CONTAINING THEM, AND FUNGICIDAL METHOD OF USING THEM

[75] Inventors: Margaret C. Shephard; Patrick J. Crowley, both of Berkshire, England

[73] Assignee: Imperial Chemical Industries PLC, London, England

[21] Appl. No.: 768,837

[22] Filed: Aug. 23, 1985

[30] Foreign Application Priority Data

Sep. 7, 1984 [GB] United Kingdom ............... 8422592

[51] Int. Cl.$^4$ ................... A01N 43/56; A01N 43/08; C07D 307/54; C07D 231/12
[52] U.S. Cl. .................... 514/406; 514/471; 548/378; 549/493; 558/300; 564/78; 564/158
[58] Field of Search ............. 548/378; 549/493; 514/406, 471

[56] References Cited

U.S. PATENT DOCUMENTS

| 4,432,784 | 2/1984 | Kay et al. | 71/88 |
|---|---|---|---|
| 4,447,446 | 5/1984 | Kay et al. | 549/436 |
| 4,515,959 | 5/1985 | Kay et al. | 548/378 |

FOREIGN PATENT DOCUMENTS 0059536  3/1985  European Pat. Off. ............ 558/300
0135304  3/1985  European Pat. Off. ............ 558/300
0149324  7/1985  European Pat. Off. ............ 558/300

OTHER PUBLICATIONS

Synthesis International Journal of Methods in Synthetic Organic Chemistry, No. 7, Jul. 1972, p. 380, Georg Thieme Verlag, Stuttgart.

*Primary Examiner*—Alan L. Rotman
*Assistant Examiner*—Kurt G. Briscoe
*Attorney, Agent, or Firm*—Cushman, Darby & Cushman

[57] ABSTRACT

An amide derivative of the formula (I):

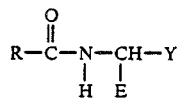

Formula I or a tautomeric form thereof, wherein
R is a phenyl group substituted in the 4-position by a group of $R^1XCH_2$-, where $R^1$ is $C_1$-$C_4$ alkyl, $C_3$-$C_4$ alkenyl, $C_3$-$C_4$ alkynyl, $C_1$-$C_4$ alkylcarbonyl, or H, and X is oxygen or sulphur;
E is CN, or $CSNH_2$, or $CONH_2$; and
Y is 1-pyrazolyl or 2-furyl. Compositions and processes for using these derivatives to combat plant fungi are also disclosed.

5 Claims, No Drawings

BENZOYLAMINOMETHYLPYRAZOLES AND FURANS, COMPOSITION CONTAINING THEM, AND FUNGICIDAL METHOD OF USING THEM

This invention relates to substituted benzamide derivatives useful as herbicides and fungicides, to processes of combating weeds and fungal infestations and to herbicidal and fungicidal compositions.

Substituted benzamide derivatives have previously been proposed for use as herbicides and fungicides, and for example, the compounds disclosed in European patent applications, publication Nos. 59536, 61836 and 76030, may be mentioned as well as UK Patent Publication No. 2152927.

We have now found that a certain, related, class of compounds possess appreciably lower phytotoxicity towards plants while maintaining high levels of fungicidal activity.

According to the present invention therefore there are provided amide derivatives of the general formula (I):

$$R-\underset{H}{\underset{|}{C}}(=O)-\underset{}{\underset{|}{N}}-\underset{E}{\underset{|}{CH}}-Y \qquad \text{Formula I}$$

wherein
- R is a phenyl group substituted in the 4-position by a group of $R^1XCH_2-$, where $R^1$ is $C_1-C_4$ alkyl, $C_3-C_4$ alkenyl, $C_3-C_4$ alkynyl, $C_1-C_4$ alkylcarbonyl, or H, and X is oxygen or sulphur;
- E is CN, or $CSNH_2$ or $CONH_2$; and
- Y is $C_1-C_4$ alkoxy, $C_3-C_4$ alkenyloxy, $C_3-C_4$ alkynyloxy, 1-pyrazolyl or 2-furyl.

The structural formula (I) given above is believed to be the one which best represents the structure of the compounds. For some compounds within the scope of the formula (I) it may be possible in principle for tautomeric forms of the compound to exist, in which a hydrogen atom is transposed to another part of the molecule and the chemical bonds between the atoms of the molecule are consequently rearranged; thus, it is possible in principle for the molecule to exist in the alternative form (II):

$$R-\underset{OH}{\underset{|}{C}}=N-\underset{E}{\underset{|}{C}}\overset{H}{\underset{}{-}}Y \qquad \text{Formula II}$$

The structural formula (I) is intended to represent and include such tautomeric forms, insofar as they may exist. The structural formula (I) is also intended to include any physically distinguishable modifications of the compounds which may arise, for example, from different ways in which the molecules are arranged in a crystal lattice, or from the inability of parts of the molecules to rotate freely in relation to other parts, or from geometrical and or optical isomerism, or from intramolecular or intermolecular bonding, or otherwise.

TABLE I

| Compound No. | R | E | Y | Mpt °C. | Preparation Method |
|---|---|---|---|---|---|
| 1 | $4-CH_3OCH_2.C_6H_4$ | $CONH_2$ | 1-pyrazolyl | 157–160 | A |
| 2 | $4-CH_3OCH_2.C_6H_4$ | CN | 1-pyrazolyl | 155–157 | A |
| 3 | $4-CH_3OCH_2.C_6H_4$ | $CSNH_2$ | 1-pyrazolyl | 113–115 | E |
| 4 | $4-C_2H_5OCH_2.C_6H_4$ | CN | 1-pyrazolyl | 156–157 | D |
| 5 | $4-C_2H_5OCH_2.C_6H_4$ | $CSNH_2$ | 1-pyrazolyl | 120–122 | E |
| 6 | $4-\underline{n}-C_3H_7OCH_2.C_6H_4$ | CN | 1-pyrazolyl | 123–125 | D |
| 7 | $4-C_2H_5OCH_2.C_6H_4$ | CN | ethoxy | 87–89 | D |
| 8 | $4-CH_3OCH_2.C_6H_4$ | CN | ethoxy | 99–100 | D |
| 9 | $4-CH_3SCH_2.C_6H_4$ | CN | 1-pyrazolyl | 111–112 | D |
| 10 | $4-CH_2=CHCH_2OCH_2.C_6H_4$ | CN | 1-pyrazolyl | | |
| 11 | $4-CH\equiv CCH_2OCH_2.C_6H_4$ | CN | 1-pyrazolyl | | |
| 12 | $4-CH_2=CHCH_2OCH_2.C_6H_4$ | $CSNH_2$ | 1-pyrazolyl | | |
| 13 | $4-CH\equiv CCH_2OCH_2.C_6H_4$ | $CSNH_2$ | 1-pyrazolyl | | |
| 14 | $4-CH_2=CHCH_2OCH_2.C_6H_4$ | CN | ethoxy | | |
| 15 | $4-CH\equiv CCH_2OCH_2.C_6H_4$ | CN | ethoxy | | |
| 16 | $4-CH_3OCH_2.C_6H_4$ | CN | propargyloxy | | |
| 17 | $4-CH_3OCH_2.C_6H_4$ | CN | 2-furyl | | |

The invention further provides processes for preparing compounds of formula (I) above. Thus the compounds may be prepared, for example, by the process of Scheme A below:

Scheme A (a) $RCOCl + NH_2CH_2CN \longrightarrow RCONHCH_2CN$
(III)

(b) $(III) + \text{brominating agent} \longrightarrow RCONHCHCONH_2$ with Br substituent
(IV)

(c) $(IV) + YH \longrightarrow RCONHCH(Y)(CONH_2)$
(V)

(d) $(V) + \text{dehydrating agent} \longrightarrow RCONH-CH(Y)(CN)$
(VI)

The process outlined schematically in Scheme A above begins with step (a), in which an acid chloride RCOCl is reacted with amino-acetonitrile by a conventional procedure to obtain the acylaminoacetonitrile derivative (III). This is then reacted in step (b) with a brominating agent (for example bromine in glacial acetic acid) to give the brominated derivative (IV). This bromination procedure also simultaneously hydrates the cyano group to a carbamoyl group —CONH$_2$, and necessitates treatment with a dehydrating agent at a later stage to convert the carbamoyl group back into a cyano group. It may be possible to avoid the undesired conversion of the cyano group to carbamoyl by use of a different solvent or brominating agent and thereby shorten the process by making step (d) unnecessary.

In step (c), the bromo compound (IV) is reacted with an appropriate nucleophile of formula YH to obtain the carbamoyl compound (V). Preferably the reaction is carried out in a solvent; the solvent should be an aprotic solvent to avoid reaction of the solvent with the bromo-compound (IV). Preferably an acid acceptor is present in at least a stoichiometric proportion. Examples of acid acceptors include tertiary amines, for example triethylamine and pyridine. The reaction takes place readily even at ambient temperatures but may be accelerated if desired by heating for example to 100° C. or above.

The intermediate compounds of formula IV and V are novel and constitute a further aspect of the present invention.

The final step (d) of Scheme A is the treatment of the carbamoyl compound (V) with a dehydrating agent to convert it to the corresponding cyano compound. The dehydrating agent may be, for example, a bi-molar amount of p-toluene sulphonyl chloride in pyridine as solvent and acid acceptor, or another dehydrating agent, for example phosphorus oxychloride-dimethylformamide. The reaction with p-toluenesulphonyl chloride proceeds readily at ambient temperature. Scheme A has been described in terms of brominated compounds; however, the scheme could equally be carried out using a chlorinating agent (eg. gaseous chlorine) in place of a brominating agent, to produce the chlorinated compound corresponding to compound (IV); this could then be used in step (c) in place of compound (IV). This route cannot be used where R is readily attacked by elemental bromine or chlorine.

A further process for making compounds of the invention is outlined in Scheme B, wherein R$^2$ is C$_1$–C$_6$ alkyl:

Scheme B

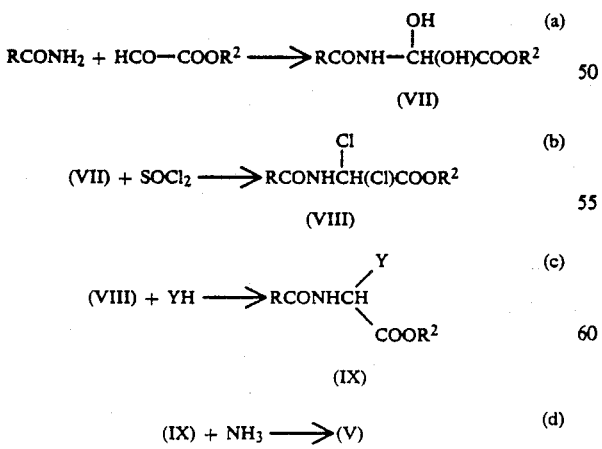

In step (a) of Scheme B, an amide RCONH$_2$ is condensed with a glyoxylic ester HCO—COOR$^2$ to give the hydroxy intermediate (VII). The group R$^2$ is an ester radical, for example an alkyl group of 1 to 4 carbon atoms (eg. a methyl group). In step (b), the hydroxy intermediate (VII) is treated with a chlorinating agent (eg. thionyl chloride) to convert it to the chloro-derivative (VIII). This is in turn reacted in step (c) with the appropriate nucleophile, YH, to give the ester (IX). Treatment of this with ammonia in step (d) gives the carbamoyl derivative (V) which may then be converted to the cyano compound of the invention by the method of step (d) of Scheme A.

A further process for making the compounds of the invention is outlined in Scheme C below.

Scheme C

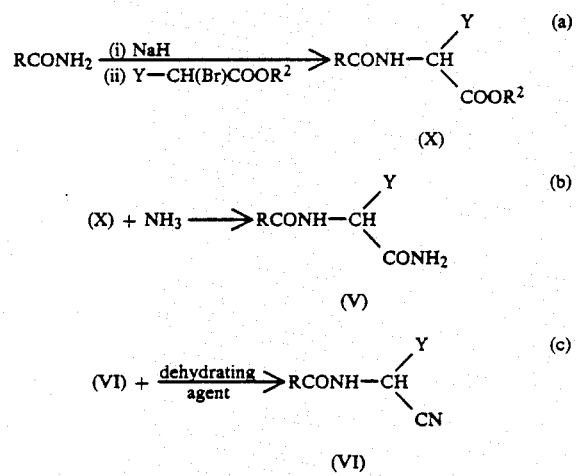

According to Scheme C, an amide RCONH$_2$ is first treated with sodium hydride and the anion so generated is then reacted with an alpha bromo ester Y—CH(Br)COOR$^2$ to give the ester (X). This is then reacted with ammonia to give the amide (V), and finally (V) is treated with a dehydrating agent to give the nitrile (VI).

A further method for preparing compounds of the invention is outlined in Scheme D.

Scheme D

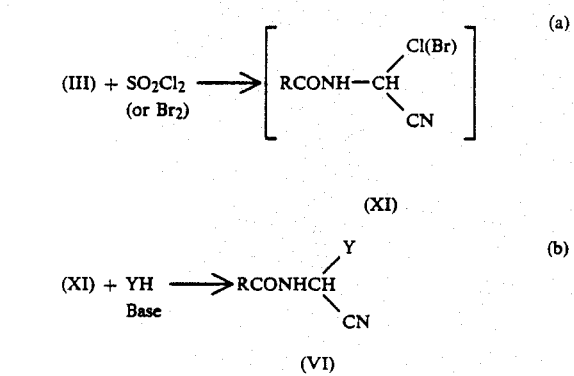

According to Scheme D (III) is chlorinated (eg. with SO$_2$Cl$_2$) or brominated (eg. with Br$_2$) in an aprotic solvent to give the highly reactive bromo- or chloro-derivative (XI). This is treated with the appropriate nucleophile YH in the presence of base to give the required nitrile (VI).

The chloro- or bromo-nitriles (XI) are too unstable to be isolated and characterised, and are used within a short time after they are prepared. The final stage (b) of the scheme may conveniently be carried out by using an excess of the nucleophile YH, and anhydrous potassium carbonate as the base. Triethylamine or other tertiary amines may also be used as the base.

Compounds of the invention in which the group E is a thiocarbamoyl radical may be prepared according to Scheme E below:

Scheme E

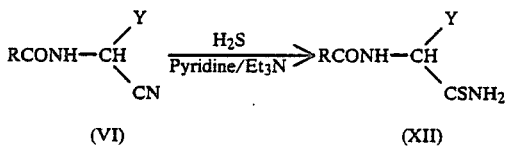

(VI)                   (XII)

The reaction is conveniently carried out by passing gaseous $H_2S$ through a solution of the nitrile (VI) in a suitable solvent such as toluene or pyridine containing a little triethylamine as catalyst. Usually the solution is externally cooled to 0°–10°. If the product (XII) does not separate from the solution, it may be isolated by removal of the solvent.

The amide derivatives of formula I, and compositions containing them, are variously active against a wide range of fungal diseases, particularly, for example, against:

*Plasmopara viticola* (downy mildew) on vines and
*Phytophthora infestans* (late blight) on potatoes and tomatoes and other species of Phytophthora
*Phytophthora parasitica, Phytophthora cinnamomi, Phytophthora palmivora* and *Phytophthora capsici* on a range of commercially important crops
Pseudoperonospora cubensis on cucurbits
*Peronospora tabacina* on tobacco
*Peronospora parasitica* on cabbage
*Peronospora destructor* on onions
*Bremia lactuca* on lettuce
Pythium species on a range of commercially important crops
Other downy mildews and other fungal diseases, for example:
*Venturia inaequalis* (scab) on apples
*Pyricularia oryzae* on rice
*Cercospora arachidicola* on peanuts and other
Cercospora species.

A particularly valuable feature of the activity of the amide derivatives is their systemic effect, ie. their ability to move in a plant to combat an infection or infestation remote from the site of initial application. Thus a derivative, or a composition containing it, may be applied to the soil surrounding the roots of a plant or to the seed or to other plant areas, eg. leaves, and be taken up by the plant through its roots, or other areas, to combat fungi locally or elsewhere on the plants.

In another aspect, therefore, the invention provides a process for combatting fungi, especially of inhibiting the growth of fungi on plants, which comprises applying to the plants, or the locus thereof, a fungicidally effective amount of a compound of the formula (I) as hereinbefore defined. The amount of the compound may vary, depending upon the identity of the particular compound chosen, the fungal species whose growth is to be inhibited, and the plant or locus involved.

The skilled worker in the fungicide art will readily be able to establish appropriate application rates by standard procedures without undue experimentation.

Preferred compounds for use in the fungicidal compositions of the invention and the process for combatting fungi are those defined in detail above with reference to formula I wherein R is optionally-substituted phenyl, especially 4-methoxymethylphenyl, Y is pyrazolyl and E is CN or $CSNH_2$.

The compounds used in the process and compositions of the invention are preferably applied in the form of a composition, in which the active ingredient is mixed with a carrier comprising a solid or liquid diluent. In another aspect, therefore, the invention provides a fungicidal composition, comprising as an active ingredient a compound of the formula (I) as hereinbefore defined, in admixture with a solid or liquid diluent. Preferably the composition also comprises a surface-active agent.

The amide derivatives may be used as such for antifungal purposes but are more conveniently formulated into compositions for such usage.

The invention also provides fungicidal compositions comprising as active ingredient an amide derivative as defined in any of the paragraphs above.

The amide derivatives and compositions containing them can be used to combat plant fungi and treat plants or seeds in a number of ways, for example they can be applied, formulated or unformulated, directly to the foliage of a plant which is infected or likely to become infected, or they can be applied also to bushes and trees, to soil or to other medium in which plants, bushes or trees are growing or to be planted, or they can be sprayed on, dusted on or applied as a cream or paste formulation. Application can be to any part of the plant, bush or tree, for example to the foliage, stems, branches, seeds or roots, or to the soil surrounding the roots.

The terms "combatting" and "treatment" as used herein embrace all the foregoing modes of application and the term "plant" includes seedlings, bushes and trees. Furthermore, the method of the invention includes protectant, prophylactic and eradicant treatment.

The derivatives are preferably used for agricultural and horticultural purposes in the form of compositions. The type of composition used in any instance will depend upon the particular purpose envisaged.

The compositions may be in the form of dusting powders or granules, for example ordinary grains or "slow release" granules wherein the active ingredient is mixed with a solid diluent or carrier, for example, kaolin, bentonite, kieselguhr, dolomite, calcium carbonate, talc, powdered magnesia, Fuller's earth, gypsum, Hewitt's earth, diatomaceous earth and China clay.

Compositions for dressing seed may, for example, comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersion of emulsions may be prepared by dissolving the active ingredient(s) in an organic solvent which may contain wetting, dispersing or emulsifying agent(s) and then adding the mixture so obtained to water which may also contain wetting, dispersing or emulsifying agent(s). Suitable organic solvents are ethylene dichloride, isopropyl alcohol, propylene glycol, diacetone alcohol, toluene, kerosene, methylnaphthalene, xylenes and trichloroethylene.

The compositions for spraying may also be in the form of aerosols wherein the formulation is held in a propellant, eg. fluorotrichloromethane or dichlorodifluoromethane.

By including suitable additives, for example additives for improving the distribution, adhesive power and resistance to rain on treated surfaces, the different compositions can be better adapted for various utilities.

The derivatives can be used in smoke generators and also as mixtures with fertilisers (eg. nitrogen- or phosphorus-containing fertilisers). Compositions comprising only granules of fertiliser incorporating, for example coated with, the derivative, are preferred.

The invention therefore also provides a fertiliser composition comprising the derivative and a fertiliser.

The compositions may also be in the form of liquid preparations for use as dips or sprays which are generally aqueous dispersions or emulsions containing the active ingredient in the presence of one or more surface active agent(s), dispersing agent(s), emulsifying agent(s) or anionic or non-ionic agents. Suitable cationic agents are quaternary ammonium compounds for example, cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzene-sulphonate, sodium, calcium or ammonium lignosulphonate, butyl-naphthalene sulphonate, and a mixture of sodium di-isopropyl- and triisopropylnapththalene sulphonates).

Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene ocide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such form aqueous preparations which remain homogenous for a sufficient time to enable them to be applied by conventional spray equipment. The concentrates may conveniently contain 10–85%, generally 25–60%, by weight of the active ingredient(s).

When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, eg. compounds having similar or complementary fungicidal or plant growth regulating activity or compounds having herbicidal or insecticidal activity.

The other fungicidal compound can be for example one which is capable of combating ear diseases of cereals (eg. wheat) such as Septoria, Gibberella and Helminthosporium spp., seed and soil borne diseases and downy and powdery mildews and Botrytis on grapes and powdery mildew and scab on apple etc or cercospora on a variety of crops, or other diseases such as *Cercosporella herpotrichoides* on cereals. These mixtures of fungicides can have a broader spectrum of activity than the compound of general formula (I) alone; further the other fungicide can have a synergistic effect of the fungicidal activity of the compound of general formula (I). Examples of the other fungicidal compound are imazalil, benomyl, carbendazim (BCM), thiophanate-methyl, captafol, folpet, captan, sulphur, carbamates, dithiocarbamates, phenyl-tin compounds, carbathiins, dicarboximides (including iprodione, vinclozolin, procymidone), copper oxychloride, triforine, dodemorph, tridemorph, dithianon, pyrazophos, binapacryl, quinomethionate, panoctine, furalaxyl, aluminium tris-(ethylphosphonate), cymoxanil, ethirimol, dimethirimol, fenarimol, fenpropidin, fenpropimorph, propiconazole, bupirimate, metalaxyl, ofurace, benalaxyl, oxadixyl, chlorothalonil, metaxanine, triazole derivatives such as triadimefon, triadimenol, diclobutrazol, flutriafol and penconazole and ergosterol-synthesis inhibiting fungicides other than those here disclosed.

Suitable insecticides are pirimor, croneton, dimethoate, metasystox, formothion, and pyrethroid compounds.

The other plant growth regulating compound can be one which controls weeds or seedhead formation, improves the level of longevity of the plant growth regulating activity of the compounds of general formula (I), selectively controls the growth of the less desirable plants (eg. grasses) or causes the compound of general formula (I) to act faster or slower as a plant growth regulating agent. Some of these other agents will be herbicides. Examples of suitable agents are the gibberellins (eg. GA$_3$, GA$_4$ or GA$_7$), the auxins (eg. indoleacetic acid, indolebutyric acid, naphthoxyacetic acid or naphthylacetic acid), the cytokinins (eg. kinetin, diphenylurea, benzimidazole, benzyladenine or BAP), phenoxyacetic acids (eg. 2,4-D or MCPA), substituted benzoic acids (eg. TIBA), morphactins (eg. chlorfluorecol), maleic hydrazide, glyphosate, glyphosine, long chain fatty alcohols and acids (eg. Off Shoot O of Off Shoot T), dikegulac, Sustar, Embark, substituted quaternary ammonium and phosphonium compounds (eg. CCC or Phosfon-D), Ethrel, carbetamide, Racuza, Alar, asulam, abscissic acid, isopyrimol, RH531, hydroxybenzonitriles (eg. bromoxynil), Avenge, Suffix or Lontrel.

The invention is illustrated by the following Examples, in which unless otherwise stated all parts are by weight and temperatures in degrees Centigrade. The Examples that describe chemical syntheses give details in some cases of the nuclear magnetic resonance (NMR) spectra of the compounds. The information given is the chemical shift ( ) for each peak in the spectrum together with a symbol to indicate the nature of the peak, as follows: s(singlet); d(doublet); m(multiplet); q(quartet); t(triplet). The solvent used was fully deuterated dimethyl sulphoxide or deuterochloroform (CDCl$_3$). Information is also given on infra-red (IR) spectra of the compounds. The information given is the transmission for each peak together with a symbol to indicate the size of the peak; s(strong); w(weak).

EXAMPLE 1

This Example illustrates the preparation of compound No 1 of Table I.

Stage 1—The Preparation of:

(4-Methoxymethylbenzoylamino)-acetonitrile

Sodium hydroxide (18.868, 0.47M) was dissolved in water (150 ml) and added to a stirred mixture of aminoacetonitrile bisulphate (24.23 g, 0.157M) and 4-methoxymethyl benzoyl chloride (29.9 g, 0.157M) in ethyl acetate (150 ml). The reaction was stirred for 2½ hours at room temperature, the ethyl acetate layer was separated off and the aqueous layer re-extracted with ethyl acetate. The ethyl acetate extracts were combined, dried over magnesium sulphate and evaporated to give a white solid. This was recrystallised from chloroform 80:100 petrol to give white plates, (24.5 gm), mpt 107°–108° C.

IR (nujol)cm$^{-1}$ 3260 (S), 1650 (S).

NMR (CDCl$_3$) 3.3(s, 3H), 4.18(d, 2H) 4.35(s, 2H) 7.12(d, 2H) 7.52(d, 2H), 7.60(m, 1H).

Stage 2—The Preparation of:

2-(4-Methoxymethylbenzoylamino)-2-(bromo)-acetamide

The acetonitrile from the previous reaction (15.0 g, 0.0735M) was dissolved in glacial acetic acid (150 ml) and stirred at room temperature, whilst adding bromine (11.76 g, 0.0735M) over 30 seconds. The resulting brown solution decolourised almost immediately and was followed by a 20° exotherm by which time a solid had precipitated. After stirring for one hour the solid was filtered and washed with acetic acid and then ether, to give a pinkish solid, which was used directly for the next reaction.

Stage 3—The Preparation of:

2-(4-Methoxymethylbenzoylamino)-2-(1-pyrazolyl)-acetamide (Compound No 1 of Table I). The amide (13.0 g, 0.043M) was added portionwise to a stirred solution of Pyrazole (3.16 g, 0.046M) in pyridine (70 ml). The resulting brown solution was stirred at room temperature for 2 hours and then overnight. The pyridine was evaporated and the resulting oil diluted with water (100 ml). On scratching a solid was obtained, which was filtered, washed with water and then ether, to give a pale orange solid (8.5 gm), mpt 157°–160° C.

IR (nujol) 3430, 3260, 1695, 1660 cm$^{-1}$.

NMR (10%CDCl$_3$ in d$^6$ DMSO), 3.40(s, 3H), 4.50(s, 2H), 6.28(m, 1H), 6.86(d, 1H), 7.16–7.64(m, 4H), 7.88–8.02(m, 2H), 9.14(d, 1H).

EXAMPLE 2

This Example illustrates the preparation of:

2-(4-Methoxymethylbenzoylamino-2-(1-pyrazolyl)-acetonitrile (Compound No 2 of Table I). Phosphoryl chloride (2.0 ml, 0.022M) was added dropwise to stirred dry DMF (10 ml) at 0° C. After 30 minutes the clear pale yellow solution was added dropwise to a stirred solution of the amide from the preceding reaction (5.0 g, 0.0174M) in dry DMF (10 ml) at −25° C. The mixture was stirred at −20° C. for one hour and then allowed to warm to −10° C. and then poured into a mixture of water (200 ml) and ether (150 ml). After shaking for a while the solid was filtered dissolved in chloroform, aded to the ether extract, and the mixture dried over magnesium sulphate. After evaporation an orange solid (1.7 g) was obtained, which was recrystallised from chloroform/petrol to give an off-white crystalline solid (1.15 g), mpt 155°–7° C.

IR (nujol)γ3250, 1665 cm$^{-1}$.

NMR (d$^6$DMSO+a trace of CDCl$_3$), 3.35(s, 3H), 4.50(s, 2H), 6.39(m, 1H), 7.44(d, 1H), 7.50–7.68(m, 3H), 7.92–8.08(m, 3H).

Microanalysis

|  | C | H | N |
|---|---|---|---|
| Expected | 62.22 | 5.18 | 20.74 |
| Found | 61.82 | 4.96 | 20.60 |

EXAMPLE 3

This Example illustrates the preparation of:

2-(4-Methoxymethylbenzoylamino9-2-(1-pyrazolyl)-thioacetamide (Compound No 3 of Table I). The pyrazole nitrile from the previous reaction (0.25 g, 0.000925M) was sitrred as a suspension in toluene (7.5 ml). Hydrogen sulphide gas was bubbled through the solution for 5 minutes and then triethylamine (0.1 g, 0.001M) was added. Hydrogen sulphide was then bubbled through the solution for a further 20 minutes, during which the solution went clear and then a new solid was precipitated. The solid was filtered, washed with toluene and ether and air dried to give an off-white solid (0.22 gm) mpt 113°–115° C. (decomp).

IR (nujol) 3240, 3110, 1665(s) cm$^{-1}$.

NMR (d$^6$-DMSO), 3.36(s, 3H), 4.48(s, 2H), 6.24(m, 1H), 6.96(d, 1H), 7.34–7.52(m, 3H), 7.80–7.96(m, 3H), 9.00(d, 1H), 9.40–10.00(m, 2H, CSNH$_2$).

EXAMPLE 4

This Example illustrates the preparation of:

2-(4-Methoxymethylbenzoylamino)-2-(ethoxy)-acetonitrile (Compound No 8 of Table 1).

A solution of 2-(4-methoxymethylbenzoylamino)-acetonitrile (5.0 g) in dry ethyl acetate (40 ml) was treated with a couple of drops of bromine and stirred at 30° C. until initiation of the reaction occurred. The bromine was then added dropwise keeping the temperature at 25°–30° C. After completion of the addition the mixture was filtered through celite, and the filtrate treated with ethanol (5 ml), with stirring, followed by triethylamine (5.0 g), at room temperature. After completion of the addition the mixture was stirred for 5 minutes, filtered through celite, and washed with water, dried over magnesium sulphate and evaporated at less than 30° C., giving a brown oil, (5.0 g). This was purified by preparative HPLC to yield the product as white needles (1.6 g), mpt 99°–100° C.

IR (nujol) ν3280, 1660 cm$^{-1}$.

NMR (CDCl$_3$)δ1.28(t, 3H), 3.44(s, 3H), 3.75(q, 2H), 4.51(s, 2H), 6.24(d, 1H), 7.40(d, 2H), 7.58(d, 1H), 7.78(d, 2H).

EXAMPLE 5

This Example illustrates a composition according to the invention which comprises an emulsifiable concentrate. The following ingredients were thoroughly mixed to give a solution.

| | |
|---|---|
| Compound No. 1 of Table I | 10% |
| Ethylene dichloride | 40% |
| Calcium dodecylbenzenesulphate | 5% |
| "Lubrol" L | 10% |
| "Aromasol" H | 35% |

EXAMPLE 6

A composition in the form of grains readily dispersible in a liquid, eg. water, was prepared by grinding together the first three ingredients in the presence of added water and then mixing in the sodium acetate. The resultant mixture was dried and passed through a British Standard mesh sieve, size 44–100, to obtain the desired size of grains.

| | |
|---|---|
| Compound No. 2 of Table I | 50% |
| "Dispersol" T | 25% |
| "Lubrol" APN 5 | 1.5% |
| Sodium acetate | 23.5% |

EXAMPLE 7

The following ingredients were ground together to produce a powder formulation readily dispersible in liquids.

| | |
|---|---|
| Compound No. 3 of Table I | 45% |
| "Dispersol" T | 5% |
| "Lissapol" NX | 0.5% |
| "Cellofas" B600 | 2% |
| Sodium acetate | 47.5% |

EXAMPLE 8

The active ingredient was dissolved in acetone and the resultant liquid was sprayed on to the granules of china clay. The solvent was then allowed to evaporate to produce a granular composition.

| | |
|---|---|
| Compound No 1 of Table I | 5% |
| China clay granules | 95% |

EXAMPLE 9

A composition suitable for use as a seed dressing was prepared by mixing the following three ingredients.

| | |
|---|---|
| Compound No 2 of Table I | 50% |
| Mineral oil | 2% |
| Chine clay | 48% |

EXAMPLE 10

A dusting powder was prepared by mixing the active ingredient with talc.

| | |
|---|---|
| Compound No 3 of Table I | 5% |
| Talc | 95% |

EXAMPLE 11

A Col formulation was prepared by ball-milling the constituents set out below and then forming an aqueous suspension of the ground mixture with water.

| | |
|---|---|
| Compound No 1 of Table I | 40% |
| "Dispersol" T | 10% |
| "Lubrol" APN5 | 1% |
| Water | 49% |

EXAMPLE 12

A dispersible powder formulation was made by mixing together the ingredients set out below and then grinding the mixture until all were thoroughly mixed.

| | |
|---|---|
| Compound No 2 of Table I | 25% |
| "Aerosol" OT/B | 2% |
| "Dispersol" A.C. | 5% |
| China clay | 28% |
| Silica | 40% |

EXAMPLE 13

This Example illustrates the preparation of a dispersible powder formulation. The ingredients were mixed and the mixture then ground in a comminution mill.

| | |
|---|---|
| Compound No 3 of Table I | 25% |
| "PERMINAL" BX | 1% |
| "Dispersol" T | 5% |
| Polyvinylpyrrolidone | 10% |
| Silica | 25% |
| China clay | 34% |

EXAMPLE 14

The ingredients set out below were formulated into a dispersible powder by mixing then grinding the ingredients.

| | |
|---|---|
| Compound No 1 of Table I | 25% |
| "Aerosol" OT/B | 2% |
| "Dispersol" A | 5% |
| China clay | 68% |

In Examples 5 to 14 the proportions of the ingredients given are by weight and the Examples were all repeated using, as active ingredient, the other compounds of Table I.

There now follows an explanation of the compositions or substances represented by the various Trade Marks and Trade Names mentioned above.

LUBROL L: a condensate of nonyl phenol (1 mole) with ethylene oxide (13 moles).

AROMASOL H: a solvent mixture of alkylbenzenes

DISPERSOL T AND AC: a mixture of sodium sulphate and a condensate of formaldehyde with sodium naphthalene sulphonate LUBROL APN 5: a condensate of nonyl phenol (1 mole) with ethylene oxide (5.5 moles)

CELLOFAS B600: a sodium carboxymethyl cellulose thickener.

EXAMPLE 15

The compounds were tested against a variety of mainly foliar fungal diseases of plants. The techniques were as follows:

For all tests, plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliar diseases, solutions and suspensions (100 ppm ai) were sprayed on the foliage and applied to the roots of the plant via the soil. The sprays were applied to maximum retention and the root drenches to a final concentration equivalent to approximately 40 ppm ai/dry soil. Tween 20, to give a final concentration of 0.05%, was added when the sprays were applied to cereals (ai means "active ingredient").

Most were protectant tests where the compound was applied to the soil and roots and to the foliage one or two days before the plant was inoculated with the pathogen. However, in the case of the test against *Erysiphe graminis hordei* the treatment was eradicative and the compounds were applied one day after inoculation.

The foliar pathogens were applied by spraying spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:
4 = no disease
3 = trace to 5% of disease on untreated plants
2 = 6–25% of disease on untreated plants
1 = 26–59% of disease on untreated plants
0 = 60–100% of disease on untreated plants
The results are shown in Table II below.

TABLE II $$R-\underset{H}{\overset{O}{\underset{\|}{C}}}-\underset{}{\overset{}{N}}-\underset{E}{\overset{}{CH}}-Y$$

| COMPOUND NUMBER OF TABLE I | Pr | Egh | Vi | Po | Ca | Pv | Fc | Rs | Pu | Xo |
|---|---|---|---|---|---|---|---|---|---|---|
| 1 | 0 | 0 | 2 | 0 | 0 | 0 | 0 | 0 | 0 | 0 |
| 2 | 0 | 0 | 2 | 2 | 0 | 4 | 0 | 0 | 2 | 0 |
| 3 | 0 | 0 | 0 | 0 | 0 | 4 | — | 0 | — | 0 |
| 4 | 0 | 0 | 0 | 0 | 1 | 4 | — | 0 | — | 0 |
| 5 | 0 | 0 | 0 | 0 | 0 | 3 | — | 0 | — | 0 |
| 6 | 0 | 0 | 0 | 0 | 0 | 4 | — | 0 | — | 3 |
| 7 | 0 | 0 | 0 | 0 | 1 | 4 | — | 0 | — | 0 |
| 8 | 0 | 0 | 0 | 0 | 0 | 4 | — | 0 | — | 0 |
| 9 | 0 | 0 | 0 | 0 | 1 | 4 | — | 0 | — | 0 |

A dash, thus "—", in the table in any column indicates that the particular compound was not tested against that particular disease.

EXAMPLE 16

Phytotoxicity to vine seedlings

Vine seedlings growing in 7 cm pots were sprayed to run-off with the test chemicals. After 9 days the plants received a second spray with the test chemicals. After treatment the plants were kept in a growth room:

| 21° C. day | 18° C. night |
|---|---|
| 60% RH day | 95% RH night |
| 16 hour day length. | |

Eleven days after the second spray growth and phytotoxicity was assessed using arbitrary grades 0–5, where 0 = no damage and 5 = plant dead.

The results are shown in the Table below. The test was assessed 11 days after the second spray and there was a 9 days interval between sprays.

| | Mean phytotoxicity grade (3 reps)* | |
|---|---|---|
| ppm active compound in spray | Compound No 2 of Table I | Prior Art Compound A/ Compound B |
| 250 | 2.7 | 3.7 |
| 100 | 2.0 | 3.2 |
| 50 | 0.8 | 2.2 |
| Untreated | 0 | 0 |

*Arbitary grades 0 = no damage, 5 = dead.
**Compound A was not available for second spray therefore Compound B was used. (In previous tests A and B had similar phytotoxicity).

It can be concluded from this test that compound No 2 of Table I is appreciably less phytotoxic than prior art compounds A or B, particularly at the critical concentration of around 50 ppm.

The structures of prior art compounds A and B are shown below:

Prior Art Compound A

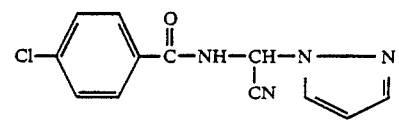

Prior Art Compound B

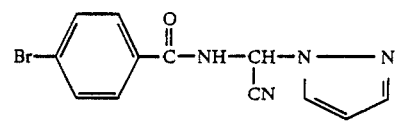

The above two compounds are disclosed in EP Patent Publication No 76030.

We claim:

1. An amide derivative of the general formula (I):

Formula I or a tautomeric form thereof, wherein
R is a phenyl group substituted in the 4-position by a group of the formula $R^1XCH_2-$, where $R^1$ is $C_1-C_4$ alkyl, $C_3-C_4$ alkenyl, $C_3-C_4$ alkynyl, $C_1-C_4$ alkylcarbonyl, or H, and X is oxygen or sulphur;
E is CN, or $CSNH_2$ or $CONH_2$; and
Y is 1-pyrazolyl or 2-furyl.

2. An amide derivative as claimed in claim 1 wherein R is a $C_{1-4}$ alkoxymethylphenyl group; E is CN or $CSNH_2$ and Y is 1-pyrazolyl.

3. The amide compound of formula
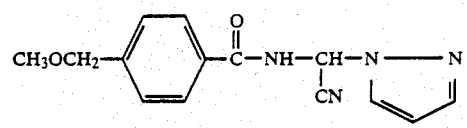
4. A fungicidal composition comprising as an active ingredient a fungicidally effective amount of an amide derivative as claimed in claim 1.
5. A method for combating fungi, which comprises applying to the plants, or the locus thereof, a fungicidally effective amount of a compound of the formula (I) as defined in claim 1.